(12) United States Patent
Huthmacher

(10) Patent No.: US 11,744,955 B2
(45) Date of Patent: Sep. 5, 2023

(54) SHEATH REMOVER AND METHODS FOR ASSEMBLY THEREOF

(71) Applicant: Sanofi-Aventis Deutschland GMBH, Frankfurt am Main (DE)

(72) Inventor: Winfried Huthmacher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/095,075

(22) Filed: Jan. 10, 2023

(65) Prior Publication Data

US 2023/0149634 A1 May 18, 2023

Related U.S. Application Data

(63) Continuation of application No. 17/738,217, filed on May 6, 2022, which is a continuation of application
(Continued)

(30) Foreign Application Priority Data

May 18, 2016 (EP) .................................... 16170070

(51) Int. Cl.
*A61M 5/32* (2006.01)

(52) U.S. Cl.
CPC ........... *A61M 5/3204* (2013.01); *A61M 5/321* (2013.01); *A61M 5/3202* (2013.01); *A61M 2207/00* (2013.01)

(58) Field of Classification Search
CPC .. A61M 5/3204; A61M 5/3202; A61M 5/321; A61M 2207/00
See application file for complete search history.

(56) References Cited

U.S. PATENT DOCUMENTS

| 5,411,486 A | 5/1995 | Zadini et al. |
| 5,928,205 A | 7/1999 | Marshall |
(Continued)

FOREIGN PATENT DOCUMENTS

| CN | 101282752 | 10/2008 |
| CN | 102781500 | 11/2012 |
(Continued)

OTHER PUBLICATIONS designtekplastics.com, "What is Overmolding?," dated Oct. 26, 2013, retrieved Nov. 22, 2021 from URL <https://designtekplastics.com/tips/what-is-overmolding/.>, 2 pages.
(Continued)

*Primary Examiner* — James D Ponton
(74) *Attorney, Agent, or Firm* — Fish & Richardson P.C.

(57) ABSTRACT

The present disclosure relates to a sheath remover for removing a protective needle sheath from a drug cartridge. The sheath remover includes a resilient ring and one or more resilient legs attached to the ring and extending in a proximal direction. Each leg includes an inwardly directed ledge arranged at a proximal end of the leg. The ring consists of a resilient material allowing inward deflection of a proximal end of the ring. The present disclosure further relates to a method for assembling and a method for using the sheath remover.

30 Claims, 5 Drawing Sheets

Related U.S. Application Data

No. 16/302,531, filed as application No. PCT/EP2017/061566 on May 15, 2017, now Pat. No. 11,344,679.

(56) References Cited

U.S. PATENT DOCUMENTS

| | | |
|---|---|---|
| 7,771,397 B1 | 8/2010 | Olson |
| 8,414,533 B2 | 4/2013 | Alexandersson |
| 9,248,245 B2 | 2/2016 | Ekman et al. |
| 10,232,116 B2 | 3/2019 | Ekman et al. |
| 10,441,728 B2 | 10/2019 | Schader et al. |
| 10,463,808 B2 | 11/2019 | Huthmacher |
| 10,646,659 B2 | 5/2020 | Huthmacher et al. |
| 10,653,850 B2 | 5/2020 | Ward et al. |
| 10,857,295 B2 | 12/2020 | Huthmacher et al. |
| 10,857,307 B2 | 12/2020 | Schader et al. |
| 10,940,272 B2 | 3/2021 | Schader et al. |
| 11,197,958 B2 | 12/2021 | Ekman et al. |
| 11,344,679 B2 * | 5/2022 | Huthmacher ....... A61M 5/3204 |
| 11,484,653 B1 | 11/2022 | Ekman et al. |
| 2005/0171484 A1 | 8/2005 | Jangula |
| 2008/0269692 A1 | 10/2008 | James et al. |
| 2013/0035645 A1 | 2/2013 | Bicknell et al. |
| 2013/0144219 A1 | 6/2013 | Evans et al. |
| 2013/0150801 A1 * | 6/2013 | Ekman ................ A61M 5/3232 604/198 |
| 2014/0243753 A1 * | 8/2014 | Bostrom ............. A61M 5/3213 604/198 |
| 2016/0022914 A1 | 1/2016 | Mounce et al. |
| 2016/0243315 A1 | 8/2016 | Perche et al. |
| 2017/0014578 A1 | 1/2017 | Bunch |
| 2019/0201633 A1 | 7/2019 | Huthmacher |
| 2020/0246551 A1 | 8/2020 | Huthmacher et al. |
| 2022/0054752 A1 | 2/2022 | Ekman et al. |
| 2022/0211946 A1 | 7/2022 | Ekman et al. |
| 2022/0323690 A1 | 10/2022 | Huthmacher |

FOREIGN PATENT DOCUMENTS

| | | |
|---|---|---|
| CN | 103153373 | 6/2013 |
| CN | 103764207 | 4/2014 |
| EP | 2878319 | 6/2015 |
| GB | 2465389 | 5/2010 |
| GB | 2469671 | 10/2010 |
| GB | 2484490 | 4/2012 |
| JP | 2009-538661 | 11/2009 |
| JP | 2014-502889 | 2/2014 |
| WO | WO 2006/009508 | 1/2006 |
| WO | WO 2007/138296 | 12/2007 |
| WO | WO 2011/043714 | 4/2011 |
| WO | WO 2011/101379 | 8/2011 |
| WO | WO 2012/049493 | 4/2012 |
| WO | WO 2012/085034 | 6/2012 |
| WO | WO 2013/006119 | 1/2013 |
| WO | WO 2015/091850 | 6/2015 |

OTHER PUBLICATIONS

International Preliminary Report on Patentability in Appln. No. PCT/EP2017/061566, dated Nov. 20, 2018, 7 pages.

International Search Report and Written Opinion in Appln. No. PCT/EP2017/061566, dated Jun. 14, 2017, 10 pages.

* cited by examiner

SHEATH REMOVER AND METHODS FOR ASSEMBLY THEREOF

CROSS REFERENCE TO RELATED APPLICATIONS

The present application is a continuation of U.S. patent application Ser. No. 17/738,217, filed on May 6, 2022, which is a continuation of U.S. patent application Ser. No. 16/302,531, filed on Nov. 16, 2018, which is the national stage entry of International Patent Application No. PCT/EP2017/061566, filed on May 15, 2017, and claims priority to Application No. EP 16170070.3, filed on May 18, 2016, the disclosures of which are incorporated herein by reference.

TECHNICAL FIELD

The disclosure generally relates to a sheath remover and to methods for assembly thereof.

BACKGROUND

Administering an injection is a process which presents a number of risks and challenges for users and healthcare professionals, both mental and physical. Pre-filled syringes having an injection needle and containing a selected dosage of a medicament for administering the medicament to a patient are known in the art. Usually, a protective needle sheath is arranged over the needle which has to be removed prior to administering the injection.

SUMMARY

The present disclosure relates to a sheath remover and methods for assembly thereof.

In the context of the present specification, a sheath remover is understood to be an element capable of engaging a protective needle sheath arranged over an injection needle which may be attached on a drug cartridge, e.g. a syringe. Furthermore, in the context of the present specification, the term "distal" refers to the direction or end of a component intended to point towards a patient's skin during an injection while the term "proximal" refers to the opposite direction or end of a component intended to point away from a patient's skin during an injection. The term "inwardly" denotes a substantially radial direction towards a longitudinal axis of a component while the term "outwardly" denotes the opposite substantially radial direction pointing away from the longitudinal axis. A sheath remover arrangement is understood to be an arrangement of parts comprising a sheath remover and at least one additional part, e.g. a cap, to which the sheath remover may be coupled.

According to one aspect, a sheath remover for removing a protective needle sheath from a drug cartridge includes a resilient ring and two or more resilient legs attached directly or indirectly to the ring and extending in a proximal direction, the legs defining a space between them to receive a protective needle sheath within, wherein each leg comprises an inwardly directed ledge arranged at a proximal end of the leg, wherein the ring consists of a resilient material allowing inward deflection of a proximal end of the ring. The ledge is adapted to engage within respective recesses at the proximal end of the protective needle sheath or proximally behind the proximal end of the protective needle sheath.

This allows for removing the protective needle sheath from the drug cartridge by pulling the sheath remover in the distal direction, in particular taking into account tolerances of all involved components, e.g. varying lengths of drug cartridges and axially varying arrangement of the protective needle sheath on the drug cartridge.

In an exemplary embodiment, the ring has a conical outer surface tapering in a distal direction.

In an exemplary embodiment, a distal end of the ring is attached to a transversal disk, wherein the resilient legs originate from the transversal disk, in particular inwardly from the ring. Thus, the legs define an external diameter which may be smaller than the external diameter defined by the proximal end of the ring. This facilitates arranging the sheath remover in a cap of a drug delivery device with a basically tubular shape which is particularly easy to mold.

In an exemplary embodiment, the ledge is hook-shaped or comprises a hook adapted to engage in a recess of a protective needle sheath.

In an exemplary embodiment, a proximal face of the ledge comprises a chamfer adapted to outwardly deflect the legs when the ledges axially abut a distal end of a protective needle sheath.

In an exemplary embodiment, a sheath remover arrangement comprises the sheath remover and a cap for a drug delivery device, the cap comprising a cylindrical proximal section and a cylindrical distal section, wherein an internal diameter of the distal section substantially equals an external diameter of the ring at its proximal end when the ring is in a relaxed state, wherein a step is arranged between the proximal section and the distal section, the step adapted to axially abut the proximal end of the ring so as to limit movement of the sheath remover in the proximal direction when the ring is received in the distal section.

In an exemplary embodiment, an internal diameter of the proximal section is equal to or greater than an external diameter of the ring at its distal end. This allows for inserting the ring of the sheath remover through a proximal end of the cap.

In an exemplary embodiment, an internal diameter of the distal section is greater than an internal diameter of the proximal section.

In an exemplary embodiment, a distal stop is arranged in the distal section, the distal stop adapted to axially abut the distal end of the ring so as to limit movement of the sheath remover in the distal direction when the ring is received in the distal section.

In an exemplary embodiment, the distal stop comprises an end plate transversally arranged in the distal section.

In an exemplary embodiment, a distance between the step and the distal stop is greater than an axial length of the ring. Thus, the ring has a stroke length for axial movement equaling a difference of the distance and the axial length. The stroke length allows for a fixed position of the sheath remover on the protective needle sheath without being restricted or forcefully limited by the cap taking into account tolerances of all involved components, e.g. varying lengths of drug cartridges, axially varying arrangement of the protective needle sheath on the drug cartridge. Furthermore, the stroke length allows for serial occurrence of forces during removal of the cap from a drug delivery device and removal of the protective needle sheath from a drug cartridge.

In an exemplary embodiment, a drug delivery device comprises a drug cartridge with an injection needle and a protective needle sheath and the above described sheath remover arrangement.

In an exemplary embodiment, a method for assembling the sheath remover arrangement comprises: Inserting the sheath remover with the distal end of the ring ahead through a proximal end of the cap, thereby inwardly deflecting the proximal end of the ring and moving the ring along the proximal section into the distal section where the proximal end of the ring relaxes.

In an exemplary embodiment, a method for using the sheath remover arrangement comprises: spreading the legs apart such that an inner diameter defined by the ledges equals to or is greater than an outer diameter of a protective needle sheath, wherein the protective needle sheath is inserted within the space defined between the legs until the ledges have arrived at a proximal end of the protective needle sheath, where the legs are allowed to relax and move inwards such that the ledges engage within respective recesses at the proximal end of the protective needle sheath or proximally behind the proximal end of the protective needle sheath.

In an exemplary embodiment, wherein the legs are allowed to partly relax and move inwards when a distal end of the protective needle sheath is inserted within the space defined between the ledges such that the ledges sit on a lateral surface of the protective needle sheath, wherein the sheath remover is moved further in the proximal direction relative to the protective needle sheath with the ledges gliding over the lateral surface until reaching the proximal end of the protective needle sheath.

In an exemplary embodiment, the legs are spread apart by chamfers on the ledges and/or chamfers on the protective needle sheath when the ledges axially abut the distal end of the protective needle sheath as the sheath remover is moved in the proximal direction relative to the protective needle sheath such that the ledges sit on a lateral surface of the protective needle sheath, wherein the sheath remover is moved further in the proximal direction relative to the protective needle sheath with the ledges gliding over the lateral surface until reaching the proximal end of the protective needle sheath.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
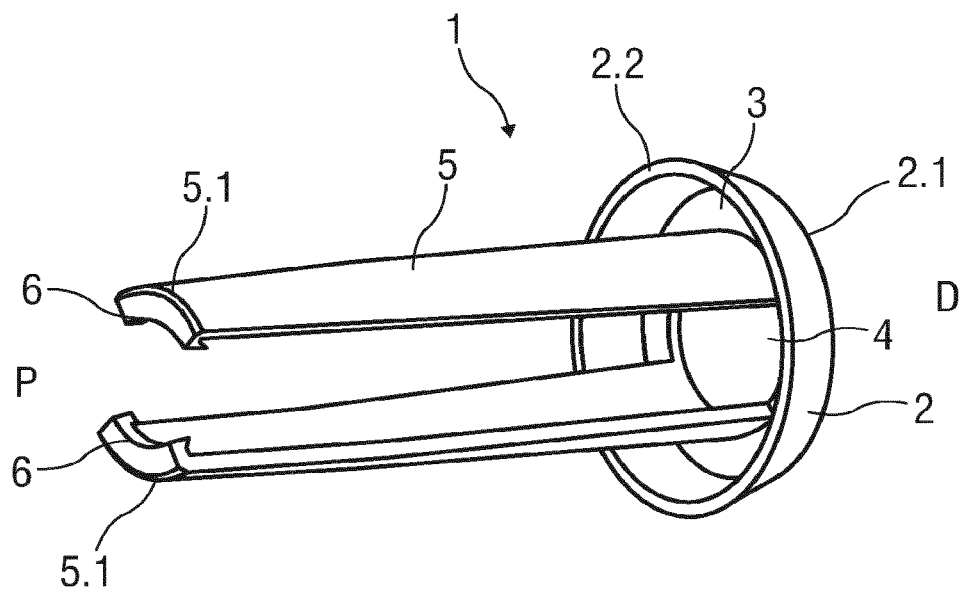
FIG. 1 is a schematic perspective view of an exemplary embodiment of a sheath remover for removing a protective needle sheath from a drug cartridge.

FIG. 1 is a schematic perspective view of an exemplary embodiment of a sheath remover 1 for removing a protective needle sheath from a drug cartridge (not shown). The sheath remover 1 comprises a ring 2 which may have a conical outer surface tapering in a distal direction D. A distal end 2.1 of the ring 2 is attached to a transversal disk 3. In an exemplary embodiment, the transversal disk 3 exhibits a central aperture 4. Two resilient longitudinal legs 5 originate from the transversal disk 3, in particular from adjacent the central aperture 4, and extend in a proximal direction P. Each leg 5 comprises an inwardly directed ledge 6 arranged at a proximal end 5.1 of the leg 5. The ledge 6 may be hook-shaped or comprise a hook as shown in FIG. 1. The sheath remover 1, in particular the ring 2 thereof, consists of a resilient material allowing for inwardly deflecting a proximal end 2.2 of the ring 2 or the entire ring 2.

In other, not shown embodiments, the ledge 6 may just comprise an inwardly directed transversal protrusion. In other, not shown embodiments, a different number of legs 5 and ledges 6 may be arranged, e.g. one leg 5 or three or more legs 5. The legs 5 define a space between them wide enough to receive a protective needle sheath within. Likewise, in other not shown embodiments, the sheath remover 1 may not have a transversal disk 3 and the legs 5 may directly originate from the distal end 2.1 of the ring 2.

In an exemplary embodiment, the legs 5 define an external diameter which may be smaller than the external diameter defined by the proximal end 2.2 of the ring 2. This facilitates arranging the sheath remover 1 in a cap of a drug delivery device with a basically tubular shape which is particularly easy to mold.

Figure 2:
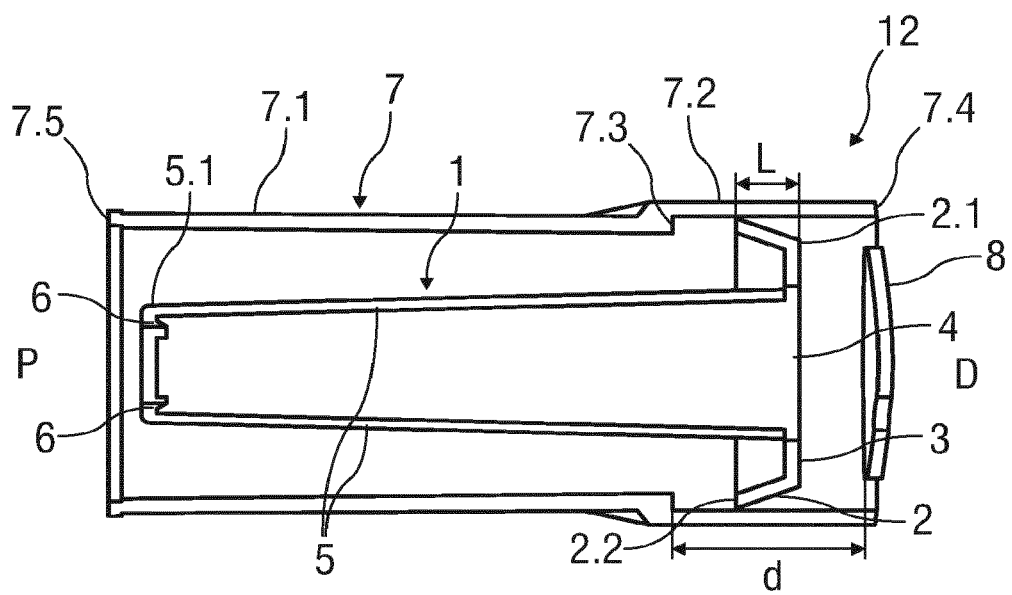
FIG. 2 is a schematic longitudinal section of the sheath remover mounted inside a cap.

FIG. 2 is a schematic longitudinal section of a sheath remover arrangement 12 comprising the sheath remover 1 mounted inside a cap 7 for a drug delivery device (not shown). The cap 7 has a tubular shape comprising a cylindrical proximal section 7.1 and a cylindrical distal section 7.2, wherein an internal diameter of the distal section 7.2 is greater than an internal diameter of the proximal section 7.1. The internal diameter of the distal section 7.2 may substantially equal an external diameter of the ring 2 at its proximal end 2.2, when the ring 2 is in a relaxed state, i.e. not inwardly deflected. The ring 2 may thus be received in the distal section 7.2 of the cap 7. In an exemplary embodiment, the internal diameter of the distal section 7.2 may be slightly greater than the external diameter of the ring 2 at its proximal end 2.2.

The internal diameter of the proximal section 7.1 may be equal to or greater than an external diameter of the ring 2 at its distal end 2.1.

A step 7.3 may be arranged between the proximal section 7.1 and the distal section 7.2, the step 7.3 adapted to axially abut the proximal end 2.2 of the ring 2 so as to limit movement of the sheath remover 1 in the proximal direction P when the sheath remover 1 is received in the distal section 7.2. A distal stop 8 may be arranged in the distal section 7.2, e.g. having the form of an end plate transversally arranged in the distal section 7.2, in particular at a distal end 7.4 thereof, the distal stop 8 adapted to axially abut the distal end 2.1 of the ring 2 so as to limit movement of the sheath remover 1 in the distal direction D when the sheath remover 1 is received in the distal section 7.2.

A distance d between the step 7.3 and the distal stop 8 may be greater than an axial length L of the ring 2 such that the ring has a stroke length S for axial movement equaling a difference of the distance d and the axial length S. The stroke length S allows for a fixed position of the sheath remover 1 on the protective needle sheath without being restricted or forcefully limited by the cap 7 taking into account tolerances of all involved components, e.g. varying lengths of drug cartridges. Furthermore, the stroke length S allows for serial occurrence of forces during removal of the cap 7 from a drug delivery device and removal of the protective needle sheath from a drug cartridge.

Instead of the step 7.3, one, two or more inward protrusions may be arranged within the cap 7 to limit movement of the sheath remover 1 in the proximal direction P when the sheath remover 1 is received in the distal section 7.2. The internal diameters of the proximal section 7.1 and the distal section 7.2 may be the same when one or more inward protrusions are arranged instead of the step 7.3. Instead of the end plate, one, two or more inward protrusions may be arranged as the distal stop 8 within the cap 7 to limit movement of the sheath remover 1 in the distal direction D when the sheath remover 1 is received in the distal section 7.2.

The sheath remover 1 may be assembled into the cap 7 by inserting the sheath remover 1 with the distal end 2.1 of the ring ahead 2 through a proximal end 7.5 of the cap 7. The resilience of the ring 2 allows inward deflection of the proximal end 2.2 of the ring 2 such that the ring 2 may be moved along the proximal section 7.1 into the distal section 7.2 where the proximal end 2.2 of the ring 2 relaxes and thus axially abuts the step 7.3 upon an attempt to move the sheath remover 1 back in the proximal direction P.

In other embodiments, the ring 2 may not have a conical outer surface but be anyway resilient so as to be able to be inwardly deflected when passing the step 7.3 or one or more inward protrusions.

Figure 3:
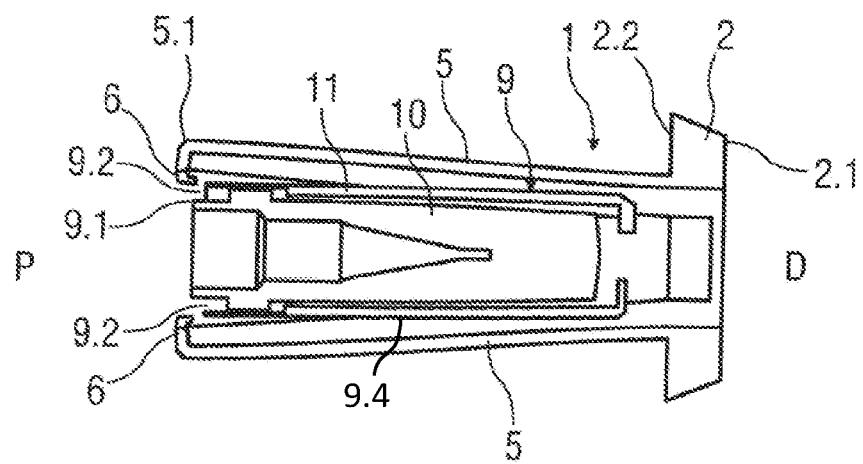
FIG. 3 is a schematic longitudinal section of the sheath remover during assembly over a protective needle sheath according to a first exemplary method.

FIG. 3 is a schematic longitudinal section of the sheath remover 1 during assembly over a protective needle sheath 9 according to a first exemplary method. The protective needle sheath 9 comprises a resilient inner needle sheath 10, e.g. consisting of rubber, and a more rigid outer needle sheath 11 arranged over the inner needle sheath 10. In other embodiments, the protective needle sheath 9 may consist of only one part.

According to the first exemplary method, the legs 5 are spread apart such that an inner diameter defined by the ledges 6 is greater than an outer diameter of the protective needle sheath 9, i.e. wide enough to allow the protective needle sheath 9 to be inserted within the space defined between the legs 5 without touching the ledges 6. When the ledges 6 have arrived at a proximal end 9.1 of the protective needle sheath 9, the legs 5 are allowed to relax and move inwards such that the ledges 6 engage within respective recesses 9.2 at the proximal end 9.1 of the protective needle sheath 9 or proximally behind the proximal end 9.1 of the protective needle sheath 9.

Figure 4:
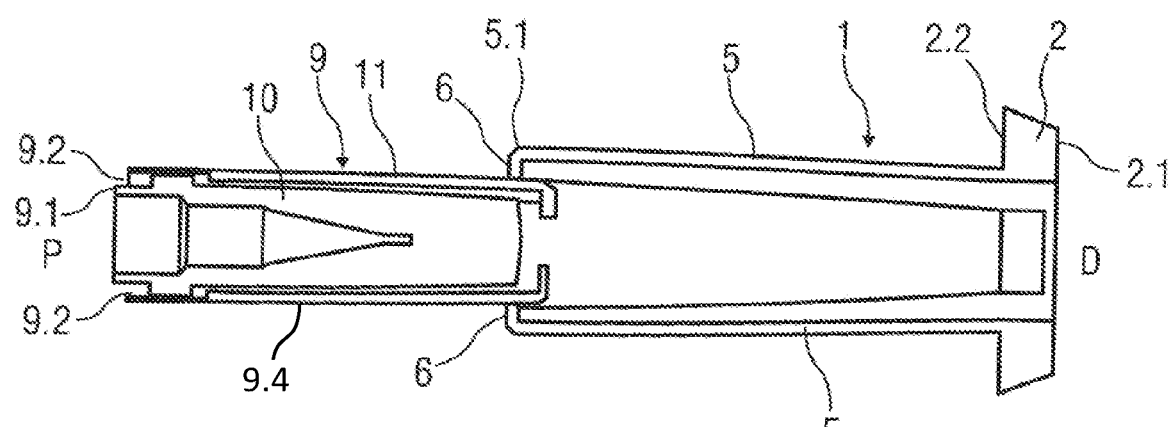
FIG. 4 is a schematic longitudinal section of the sheath remover during assembly over a protective needle sheath according to a second exemplary method.

FIG. 4 is a schematic longitudinal section of the sheath remover 1 during assembly over a protective needle sheath 9 according to a second exemplary method. The protective needle sheath 9 comprises a resilient inner needle sheath 10, e.g. consisting of rubber, and a more rigid outer needle sheath 11 arranged over the inner needle sheath 10. In other embodiments, the protective needle sheath 9 may consist of only one part.

According to the second exemplary method, the legs 5 are spread apart such that an inner diameter defined by the ledges 6 is greater than an outer diameter of the protective needle sheath 9, i.e. wide enough to allow the protective needle sheath 9 to be inserted within the space defined between the legs 5 without touching the ledges 6. As soon as a distal end 9.3 of the protective needle sheath 9 is located between the ledges 6, the legs 5 are allowed to relax and move inwards such that the ledges 6 sit on a lateral surface 9.4 of the protective needle sheath 9. As the sheath remover 1 is moved further in the proximal direction P relative to the protective needle sheath 9, the ledges 6 glide over the lateral surface 9.4 until reaching the proximal end 9.1 of the protective needle sheath 9 where they engage within respective recesses 9.2 at the proximal end 9.1 of the protective needle sheath 9 or proximally behind the proximal end 9.1 of the protective needle sheath 9 thus allowing the legs 5 to further or fully relax. The second exemplary method is particularly suitable for protective needle sheaths 9 with a smooth lateral surface 9.4, e.g. protective needle sheaths 9 comprising a more rigid outer needle sheath 11 arranged over an inner needle sheath 10.

Figure 5:
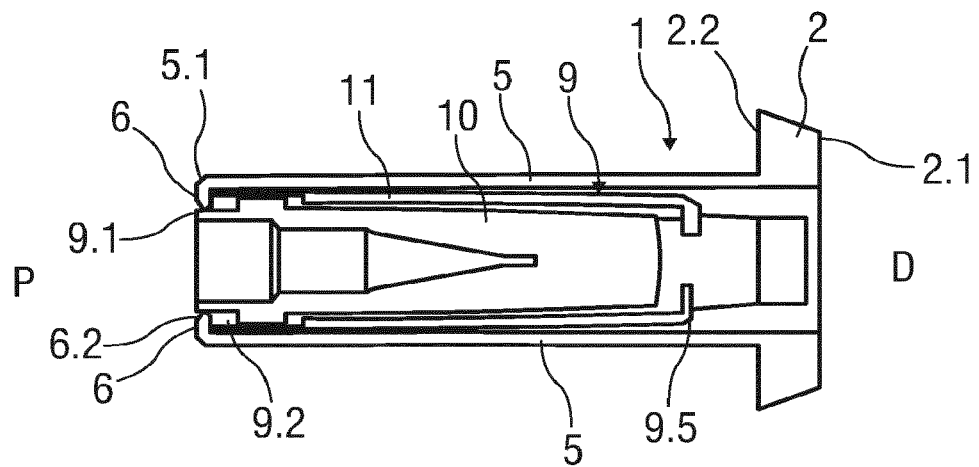
FIG. 5 is a schematic longitudinal section of the sheath remover during assembly over a protective needle sheath according to a third exemplary method.

FIG. 5 is a schematic longitudinal section of the sheath remover 1 during assembly over a protective needle sheath 9 according to a third exemplary method. The protective needle sheath 9 comprises a resilient inner needle sheath 10, e.g. consisting of rubber, and a more rigid outer needle sheath 11 arranged over the inner needle sheath 10. In other embodiments, the protective needle sheath 9 may consist of only one part.

The distal end 9.3 of the protective needle sheath 9 and/or a proximal face of the ledges 6 may comprise chamfers 9.5, 6.2 adapted to outwardly deflect the legs 5 when the ledges 6 axially abut the distal end 9.3 of the protective needle sheath 9.

According to the third exemplary method, the sheath remover 1 is moved in the proximal direction relative to the protective needle sheath 9. As the ledges 6 axially abut the distal end 9.3 of the protective needle sheath 9 during this movement, the one or more chamfers 9.5, 6.2 cause the legs 5 to spread apart such that the ledges 6 are guided onto a lateral surface 9.4 of the protective needle sheath 9. As the sheath remover 1 is moved further in the proximal direction P relative to the protective needle sheath 9, the ledges 6 glide over the lateral surface 9.4 until reaching the proximal end 9.1 of the protective needle sheath 9 where they engage within respective recesses 9.2 at the proximal end 9.1 of the protective needle sheath 9 or proximally behind the proximal end 9.1 of the protective needle sheath 9 thus allowing the legs 5 to further or fully relax. The second exemplary method is particularly suitable for protective needle sheaths 9 with a smooth lateral surface 9.4, e.g. protective needle sheaths 9 comprising a more rigid outer needle sheath 11 arranged over an inner needle sheath 10.

Figure 6:
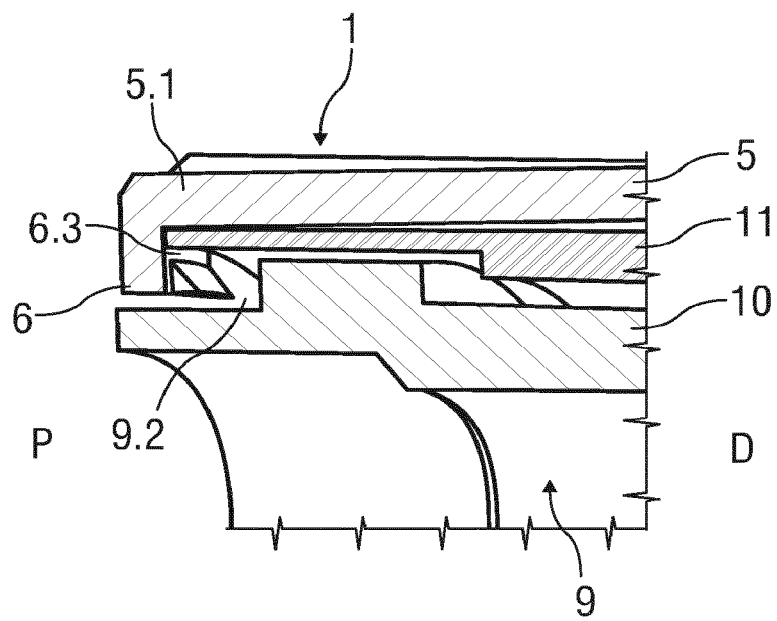
FIG. 6 is a schematic perspective detail section of the sheath remover assembled over a protective needle sheath.

FIG. 6 is a schematic perspective detail section of the sheath remover 1 assembled over a protective needle sheath 9. In the illustrated embodiment, the ledges 6 comprise a respective hook 6.3 extending from the ledge 6 in the distal direction D and adapted to engage in a recess 9.2 between the inner needle sheath 10 and the outer needle sheath 11.

Figure 7:
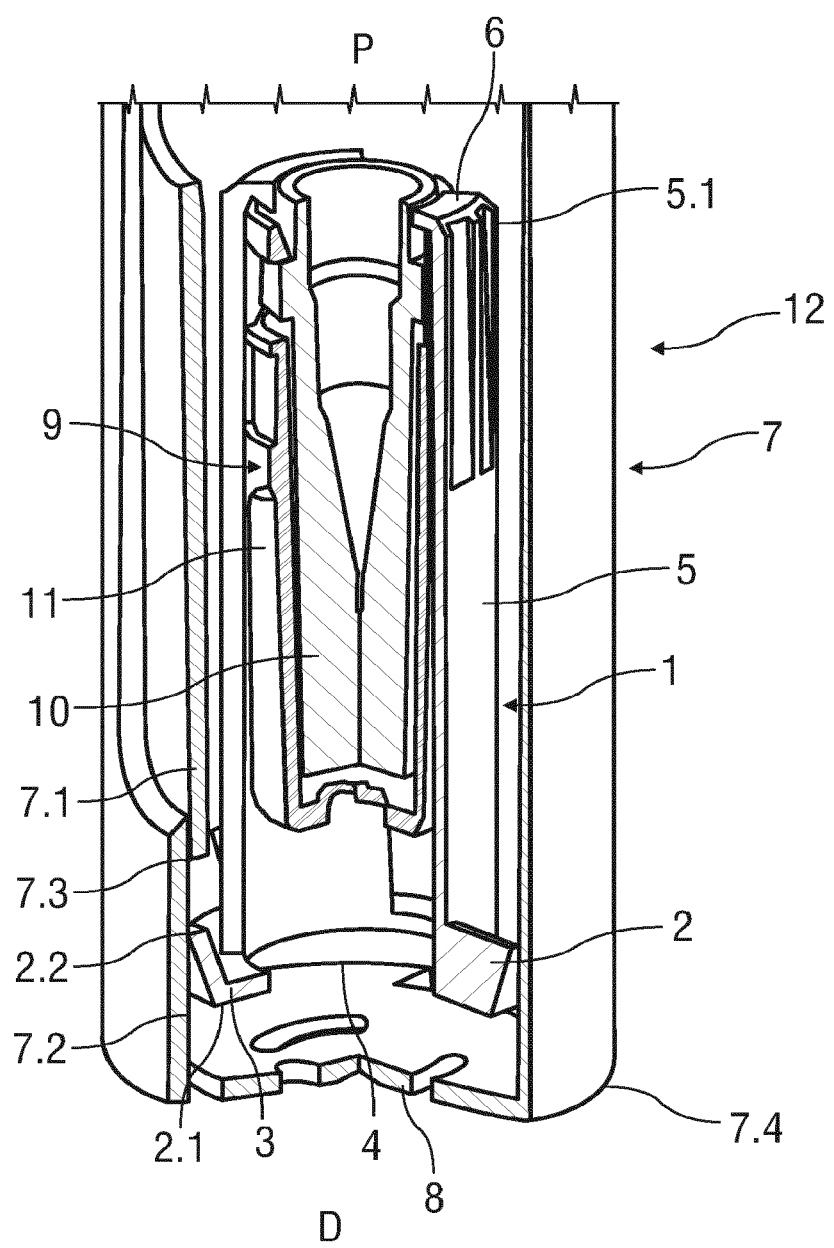
FIG. 7 is a schematic perspective section of the sheath remover assembled over a protective needle sheath and arranged within the cap.

FIG. 7 is a schematic perspective section of the sheath remover 1 assembled over a protective needle sheath 9 and arranged within the cap 7.

The illustrated embodiment as well as the methods for assembling the sheath remover 1 over the protective needle sheath 9 avoid or restrict pushing forces on the protective needle sheath 9 during assembly, transport and storage such that sterility of the protective needle sheath 9 arranged over an injection needle (not shown) is maintained.

Figure 8:
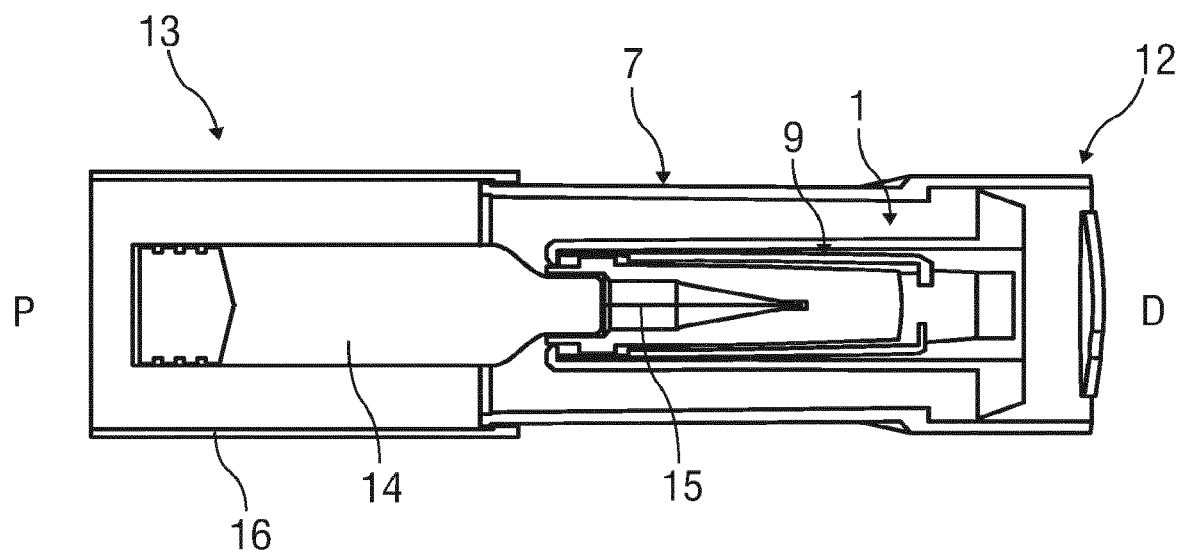
FIG. 8 is a schematic longitudinal section of a drug delivery device comprising a drug cartridge with an injection needle, a protective needle sheath and the sheath remover assembly.

FIG. 8 is a schematic longitudinal section of a drug delivery device 13 comprising a drug cartridge 14 with an injection needle 15, a protective needle sheath 9 and the sheath remover assembly 12. The drug delivery device 13 may also comprise a housing 16 adapted to contain the drug cartridge 14 and adapted to be releasably coupled to the cap 7. As the sheath remover 1 can move axially in the cap 7, the sheath remover 1 may have a fixed position on the protective needle sheath 8 without being restricted or forcefully limited by the cap 7 taking into account tolerances of all involved components, e.g. varying lengths of drug cartridges 14. The axial movement of the sheath remover 1 in the cap 7 allows for serial occurrence of forces during removal of the cap 7 from the drug delivery device 13 and removal of the protective needle sheath 8 from the drug cartridge 14.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(w-carboxyheptadecanoyl)-des(B30) human insulin and B29-N-(w-carboxyheptadecanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 sheath remover
2 ring
2.1 distal end
2.2 proximal end
3 transversal disk
4 central aperture
5 longitudinal leg
5.1 proximal end
6 ledge
6.2 chamfer
6.3 hook
7 cap
7.1 proximal section
7.2 distal section
7.3 step
7.4 distal end
7.5 proximal end
8 distal stop
9 protective needle sheath
9.1 proximal end
9.2 recess 9.3 distal end
9.4 lateral surface
9.5 chamfer
10 inner needle sheath
11 outer needle sheath
12 sheath remover arrangement
13 drug delivery device
14 drug cartridge
15 injection needle
16 housing
d distance
D distal direction
L length
P proximal direction
S stroke length

The invention claimed is:

1. A drug delivery device, comprising:
a drug cartridge with an injection needle;
a protective needle sheath configured to cover the injection needle; and
a sheath remover arrangement comprising:
a sheath remover for removing the protective needle sheath from the injection needle, the sheath remover comprising:
a ring; and
two or more resilient legs attached to the ring and extending in a proximal direction, the two or more resilient legs defining a space therebetween to receive the protective needle sheath, wherein each resilient leg of the two or more resilient legs comprises an inwardly directed projection arranged at a proximal end of the resilient leg; and
a cap comprising a proximal section, a distal section, and a step between the proximal and distal sections, wherein the ring is disposed in the distal section of the cap and the step is configured to abut a proximal end of the ring to limit proximal movement of the sheath remover relative to the cap,
wherein an internal diameter of the distal section of the cap is greater than or equal to an external diameter of the proximal end of the ring and an internal diameter of the proximal section of the cap is less than the external diameter of the proximal end of the ring.

2. The drug delivery device of claim 1, wherein each inwardly directed projection of each resilient leg of the two or more resilient legs is hook-shaped.

3. The drug delivery device of claim 1, wherein each inwardly directed projection of each resilient leg of the two or more resilient legs is adapted to engage in a recess of the protective needle sheath.

4. The drug delivery device of claim 1, wherein each inwardly directed projection of each resilient leg of the two or more resilient legs has a proximal face comprising a chamfer adapted to outwardly deflect the two or more resilient legs when each of the inwardly directed projections is proximally forced against a distal end of the protective needle sheath.

5. The drug delivery device of claim 4, wherein the two or more resilient legs are configured to relax and move inwards upon moving proximally to a position at which the inwardly directed projections of the two or more resilient legs are positioned along a proximal end of the protective needle sheath.

6. The drug delivery device of claim 5, wherein the inwardly directed projections of the two or more resilient legs are configured to engage within recesses in the proximal end of the protective needle sheath.

7. The drug delivery device of claim 1, wherein the ring is attached to a transversal disk.

8. The drug delivery device of claim 7, wherein a distal end of the ring is attached to the transversal disk.

9. The drug delivery device of claim 7, wherein the two or more resilient legs extend proximally from the transversal disk.

10. The drug delivery device of claim 1, wherein the cap comprises a distal stop configured to abut a distal end of the ring to limit distal movement of the sheath remover relative to the cap.

11. The drug delivery device of claim 10, wherein the distal stop is a distal end plate of the cap.

12. The drug delivery device of claim 10, wherein a distance between the step and the distal stop is greater than an axial length of the ring.

13. The drug delivery device of claim 1, wherein the sheath remover and the cap are configured such that the sheath remover can be inserted into the cap via an opening at a proximal end of the cap.

14. The drug delivery device of claim 13, wherein the proximal end of the ring is configured to pass through the opening at the proximal end of the cap.

15. A drug delivery device, comprising:
a drug cartridge with an injection needle;
a protective needle sheath; and
a sheath remover assembly comprising:
a sheath remover for removing the protective needle sheath from the injection needle, the sheath remover comprising:
a ring; and
two or more resilient legs attached to the ring and extending in a proximal direction, the two or more resilient legs defining a space therebetween to receive the protective needle sheath, wherein each resilient leg of the two or more resilient legs comprises an inwardly directed projection arranged at a proximal end of the resilient leg; and
a cap comprising a proximal section, a distal section, and an inward protrusion between the proximal and distal sections, wherein the ring is disposed in the distal section of the cap and the inward protrusion is configured to abut a proximal end of the ring to limit proximal movement of the sheath remover relative to the cap,
wherein an internal diameter of the distal section of the cap is greater than or equal to an external diameter of the proximal end of the ring and an internal diameter of a region of the cap comprising the inward protrusion is less than the external diameter of the proximal end of the ring.

16. The drug delivery device of claim 15, wherein each inwardly directed projection of each resilient leg of the two or more resilient legs is hook-shaped.

17. The drug delivery device of claim 15, wherein each inwardly directed projection of each resilient leg of the two or more resilient legs is adapted to engage in a recess of the protective needle sheath.

18. The drug delivery device of claim 15, wherein each inwardly directed projection of each resilient leg of the two or more resilient legs has a proximal face comprising a chamfer adapted to outwardly deflect the two or more resilient legs when each of the inwardly directed projections is proximally forced against a distal end of the protective needle sheath, and the two or more resilient legs are configured to relax and move inwards upon moving proximally to a position at which the inwardly directed projections of the two or more resilient legs are positioned along a proximal end of the protective needle sheath.

19. The drug delivery device of claim 18, wherein the inwardly directed projections of the two or more resilient legs are configured to engage within recesses in the proximal end of the protective needle sheath.

20. The drug delivery device of claim 15, wherein the ring is attached to a transversal disk.

21. The drug delivery device of claim 20, wherein the two or more resilient legs extend proximally from the transversal disk.

22. The drug delivery device of claim 15, wherein the cap comprises a distal stop configured to abut a distal end of the ring to limit distal movement of the sheath remover relative to the cap.

23. The drug delivery device of claim 22, wherein the distal stop is a distal end plate of the cap.

24. The drug delivery device of claim 22, wherein a distance between the inward protrusion and the distal stop is greater than an axial length of the ring.

25. The drug delivery device of claim 15, wherein the sheath remover and the cap are configured such that the sheath remover can be inserted into the cap via an opening at a proximal end of the cap.

26. The drug delivery device of claim 25, wherein the proximal end of the ring is configured to pass through the opening at the proximal end of the cap.

27. A drug delivery device, comprising:
a drug cartridge with an injection needle;
a protective needle sheath configured to cover the injection needle; and
a sheath remover arrangement comprising:
   a sheath remover for removing the protective needle sheath from the injection needle, the sheath remover comprising:
      a ring; and
      two or more resilient legs attached to the ring and extending in a proximal direction, the two or more resilient legs defining a space therebetween to receive the protective needle sheath, wherein each resilient leg of the two or more resilient legs comprises an inwardly directed projection arranged at a proximal end of the resilient leg; and
   a cap comprising a proximal section, a distal section, and a step between the proximal and distal sections, wherein the ring is disposed in the distal section of the cap and the cap is configured to move relative to the ring between a first position in which the step is spaced apart from a proximal end of the ring and a second position in which the step abuts the proximal end of the ring to limit proximal movement of the sheath remover relative to the cap.

28. The drug delivery device of claim 27, wherein the sheath remover is configured to move axially relative to the cap without being limited by the cap when the cap is in the first position.

29. A drug delivery device, comprising:
a drug cartridge with an injection needle;
a protective needle sheath; and
a sheath remover assembly comprising:
   a sheath remover for removing the protective needle sheath from the injection needle, the sheath remover comprising:
      a ring; and
      two or more resilient legs attached to the ring and extending in a proximal direction, the two or more resilient legs defining a space therebetween to receive the protective needle sheath, wherein each resilient leg of the two or more resilient legs comprises an inwardly directed projection arranged at a proximal end of the resilient leg; and
   a cap comprising a proximal section, a distal section, and an inward protrusion between the proximal and distal sections, the inward protrusion disposed outward of the two or more resilient legs, wherein the ring is disposed in the distal section of the cap and the inward protrusion is configured to abut a proximal end of the ring to limit proximal movement of the sheath remover relative to the cap.

30. The drug delivery device of claim 29, wherein an inner diameter of the inward protrusion is greater than an outer diameter of the two or more resilient legs.

* * * * *